United States Patent [19]

Clarke et al.

[11] 4,011,090
[45] Mar. 8, 1977

[54] AQUEOUS AMMONIACAL ZINC OXIDE COMPOSITIONS FOR LUMBER TREATMENT

[75] Inventors: Michael R. Clarke; Raman L. Desai, both of Ottawa, Canada

[73] Assignee: Canadian Patents and Development Limited, Ottawa, Canada

[22] Filed: Apr. 14, 1975

[21] Appl. No.: 567,886

Related U.S. Application Data

[63] Continuation-in-part of Ser. No. 356,355, May 2, 1973, Pat. No. 3,945,834.

[30] Foreign Application Priority Data

Sept. 1, 1972  Canada .............................. 150792

[52] U.S. Cl. ..................................... 106/15 R; 21/7; 252/8.1; 252/193; 252/380; 260/29.6 MN; 260/29.7 N; 427/331
[51] Int. Cl.$^2$ ...................... B27K 3/32; B27K 3/52; C09D 5/14
[58] Field of Search .............................. 106/15 AF

[56] References Cited

UNITED STATES PATENTS

| 2,194,827 | 3/1940 | Gordon | 106/15 AF X |
|---|---|---|---|
| 2,310,257 | 2/1943 | Ritter | 106/15 AF X |
| 2,414,661 | 1/1947 | Nikitin | 260/113 |
| 2,423,619 | 7/1947 | Roon | 106/15 AF X |
| 2,573,252 | 10/1951 | Farber | 106/15 AF X |
| 3,502,777 | 3/1970 | Burkhardt et al. | 424/293 X |
| 3,523,049 | 8/1970 | Putman | 106/15 AF X |

FOREIGN PATENTS OR APPLICATIONS

| 831,496 | 1/1970 | Canada |
|---|---|---|
| 568,393 | 1/1959 | Canada |
| 960,959 | 1/1972 | Canada |
| 898,952 | 10/1953 | Germany |
| 918,409 | 9/1954 | Germany |
| 913,356 | 4/1954 | Germany |
| 932,632 | 9/1955 | Germany |
| 139,177 | 11/1952 | Sweden |
| 182,477 | 2/1963 | Sweden |
| 1,069,640 | 5/1967 | United Kingdom |

OTHER PUBLICATIONS

Hickson's, Timber Impregnation Company, Swedish Publn. 316,287, Oct. 20, 1969.

*Primary Examiner*—Lucille M. Phynes
*Attorney, Agent, or Firm*—Flynn & Frishauf

[57] ABSTRACT

A wood treating composition is provided, comprising an aqueous solution containing (a) a specified amount of zinc ion; (b) a specified amount of ammonium thiocyanate; and (c) a specified amount of zinc oxide solubilizing amount of ammonia, the composition having a pH of 9 or more. The composition may be provided by means of an aqueous ammoniacal solution of $Zn(CNS)_2$. The composition may also include one or more of the following: (a) cupric ammonium ions, (b) a vinyl polymer latex, (c) optionally, an acidic organic surfactant compound which is soluble in the ammoniacal salt solution, or (d) an additional fungicidal agent.

10 Claims, 3 Drawing Figures

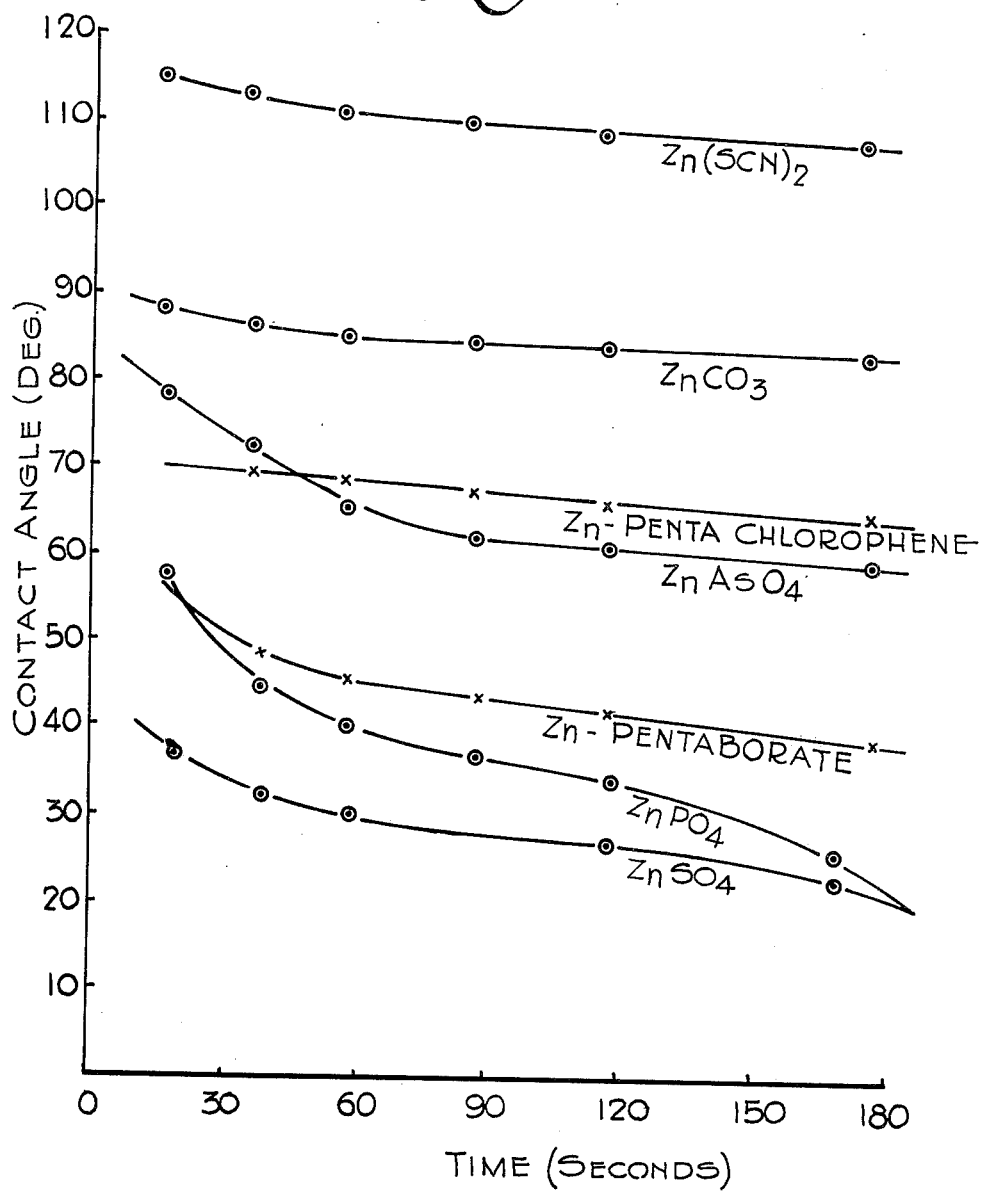

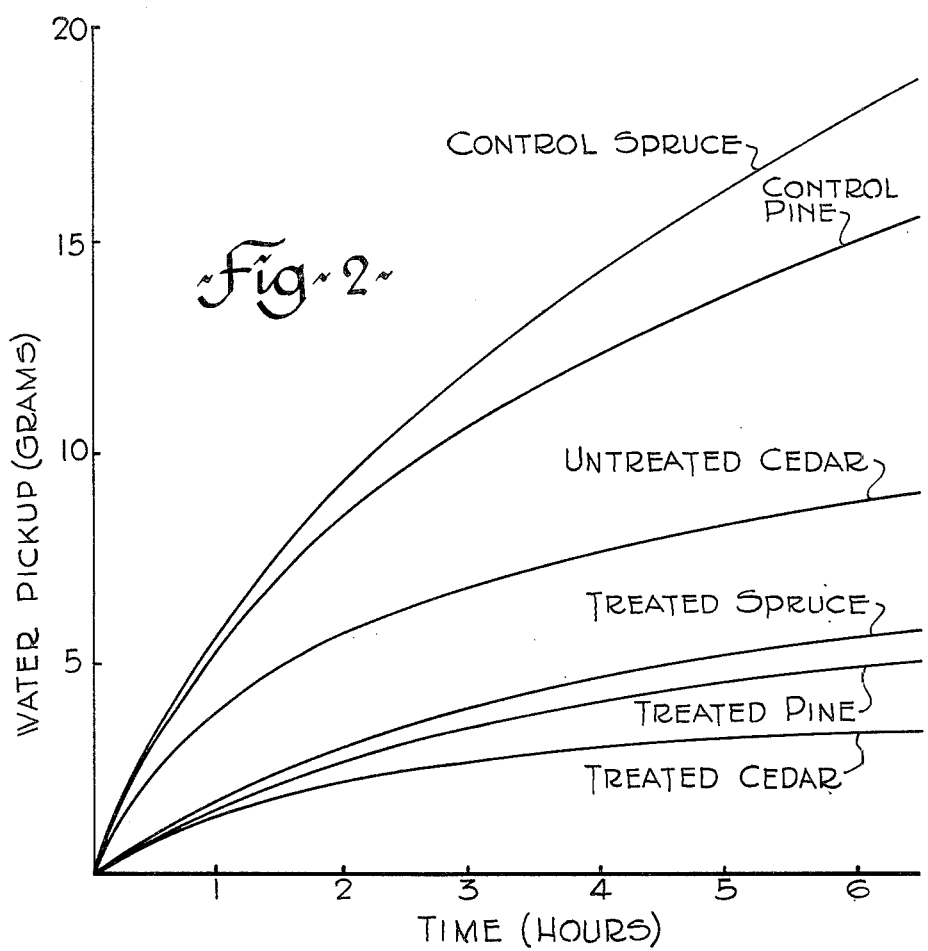
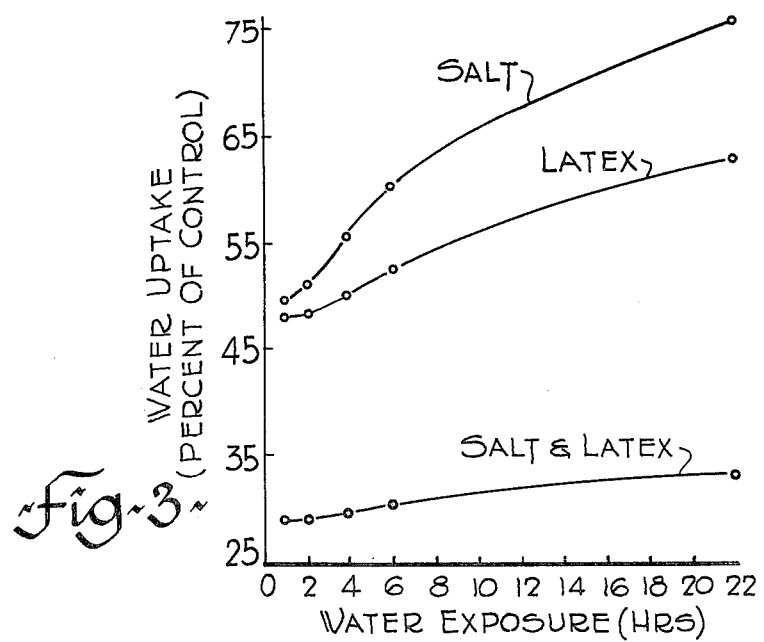

AQUEOUS AMMONIACAL ZINC OXIDE COMPOSITIONS FOR LUMBER TREATMENT

RELATED CASES

This application is a continuation-in-part of copending application Ser. No. 356,355 filed May 2, 1973 now U.S. Pat. No. 3,945,834, granted Mar. 23, 1976. This application is also related to copending application Ser. No. 362,104 filed May 27, 1973 now U.S. Pat. No. 3,945,835, granted Mar. 23, 1976 directed to arsenic-containing aqueous ammoniacal wood treating compositions.

BACKGROUND OF THE INVENTION

1. Field of the Invention

This invention relates to compositions and procedures for the treatment of wood and wood products, for protection during storage and handling of the lumber, or as a primer of sheathing. It also relates to the treated wood product so formed.

2. Description of the Prior Art

A piece of timber, due to the manner of its formation, possesses anisotropic structure which influences its properties and behaviour. Compared to competitive cladding materials, for example metals and plastics materials, it has a number of major disadvantages which tend to counteract the advantages of strength, lightness, low thermal expansion and desirable aesthetic features. To overcome and minimize these disadvantages a number of specific problems exist: the wood must be protected against degrading environmental factors (namely, moisture cycling, photodegradation and biological attack); the dimensional stability with respect to moisture cycling must be improved; photodegradation due to sunlight must be minimized; the resistance to biological attack (fungus) must be improved; the adhesion of protective and decorative coatings must be improved; and extractives which adversely affect protective and decorative properties of coatings must be sealed within the wood. All these aims should be achieved with a treatment that does not alter the natural beauty of wood.

Four classes of treatments are currently used in an attempt to meet these requirements.

The first class is that of clear or pigmented penetrating systems which contain fungicides and water-repellent additives, such as, for example, polyethylene waxes and metal stearates in a non-aqueous solvent media. These treatments are deficient in that they must be repeated at regular intervals of 1 to 2 years to provide a desired level of protection.

The second class is that of stains and sealers. These are normally synthetic resin solutions, usually pigmented and designed to penetrate the surface of the wood. These treatments as well as deficient, and should be repeated every 1 or 2 years in order to provide the required degree of protection.

The third class is that of paint systems. Such paint systems would normally consist of a primer and top coats. When well applied, these will provide the exterior cladding protection from 2 to 5 years.

The fourth class is that of salt treatments. A number of salt treatments have been suggested, the most common of which are known as copper-chrome arsenate (CCA) and acid-copper-chromate (ACC). Presently systems of this type are effective to provide relatively long term durability when applied by pressure impregnation techniques. The CCA systems are believed to become fixed in the wood by oxidation-reduction reactions associated with the chromic acid in the compositions and it is these same reactions which are believed adversely to affect stability and processing characteristics. Moreover, while providing a high level of protection against fungal attack, they provide only limited protection against weathering.

Copper and zinc containing fungicides have been proposed (see U.S. Pat. No. 2,414,661 issued Jan. 21, 1947 to A. A. Nikitin) which were prepared by precipitation from an aqueous solution of a zinc salt and a copper salt with an alkali solution containing soya bean protein, or soaps of fatty acids.

Fungicides have been proposed for cellulosic materials (see U.S. Pat. No. 2,423,619 issued July 8, 1947 to L. Roon) which comprise copper soaps formed in situ from an aqueous solution of copper salts and aqueous ammonia by reaction with fatty acids.

It has also been proposed to provide water and fire resistant coatings on wood (see U.S. Pat. No. 2,530,458 issued Nov. 21, 1950 to H. R. Frisch) by the use of zinc orthophosphate or zinc orthoarsenate compositions applied as a concentrated solution in aqueous ammonia. Zinc arsenate, zinc arsenite, and zinc phosphate can all be applied from ammonia solution and, on drying, the salt is insoluble and fixed in the wood. However, in all of these cases the weather resistance of the treated wood is not significantly improved.

It was proposed to improve the hardness, compressive strength hygroscopicity and liability to swell of wood by impregnating the wood with an aqueous ammoniacal solution of polycarboxylic acid containing at least 6 carbon atoms. (See U.S. Pat. No. 2,768,910 issued Oct. 30, 1956 to H. Krzikalla and O. Lissner).

U.S. Pat. No. 2,772,263 issued Nov. 27, 1956 to C. C. Yeager proposed to use a compound having a high fungicidal activity in wood, which is a metal rosin ammonium phenoxide, prepared by reacting a rosin ammonium phenoxide with a water soluble salt of a metal capable of forming a complex with ammonia.

U.S. Pat. No. 3,007,844 issued Nov. 7, 1961 to W. O. Schuly proposed the use of a composition comprising a heavy metal ion, borate ions and chromate ions as an impregnating agent for the preservation of wood.

U.S. Pat. No. 3,105,773 issued Oct. 1, 1963 to S. Frank and D. C. Wehner proposed to preserve wood by imparting pesticidal and anti-thallophytic properties by first impregnating the wood with a water soluble heavy metal salt, and then with an acrylic polymer solution.

Canadian Pat. No. 568,393 of Hager discloses as a wood treating composition an aqueous ammoniacal solution of copper and zinc salts with carbonate ions, and optionally also containing pentachlorophenol and/or arsenic salts.

Ammoniacal copper arsenite compositions are presently being used as presevatives.

Aims of the Invention

While the use of the compositions outlined above provided a considerable level of protection against weathering and biological attack and effectively sealed the wood and improved the adhesion of paints applied to the treated wood, the level of weather resistance achieved fell short of what was required to being the durability of wood to a level competitive with other cladding materials. None of such systems provided a suitable balanced improvement in the following requirements, namely: to impart long life to the treated wood product; to provide protection without reducing the natural appearance of the treated wood; to be capable of being applied by simple (low cost) methods of application (for example, low pressure application); and to expand the applicability of these systems which would not impart a strong colour to the treated wood. A large amount of effort has therefore been expended in modifying formulations to impart acceptable colour to the treated wood.

Therefore, prime objectives of this invention are to provide such compositions in which a suitable balanced improvement, namely for periods up to 1 year, is provided in the following properties, namely: a good level of weather resistance; low mammalian toxicity; fire retardant characteristics; resistance to biological and fungal attack; resistance to water penetration; resistance to extractive staining; adhesion properties between the wood and a coating, e.g. paint or glue, etc. later to be applied thereto; a mill treatment procedure; and no substantial adverse effect on lumber seasoning.

SUMMARY OF THE INVENTION

Broad Statements of the Invention

By one broad aspect of this invention, a wood treating composition is provided containing: (a) zinc ion, in a total amount, in the solution, of about 0.5 to about 10% by weight, as zinc; (b) ammonium thiocyanate, in an amount of about 1 to about 28% by weight, with the mole ratio calculated as $NH_4CNS/Zn$ being from about 2 to about 3; and (c) zinc thiocyanate dissolving amount of ammonia, in an amount of about 0.1 to about 28%, sufficient to provide a ratio of ammonia to zinc of from at least about 0.1 to about 1, the composition having a pH of about 9 or more.

VARIANTS OF THE INVENTION

Such composition may be provided by the following solution:

An aqueous ammoniacal solution of $Zn(CNS)_2$, preferably wherein the amount of $Zn(CNS)_2$ is about 1 to about 25% by weight, and the aqueous ammonia is at a concentration of about 1 to about 28% by weight, with a mole ratio of ammonia to zinc being at least 0.1 up to about 1.

By another aspect of this invention, a first modified composition includes, additionally, copper, as cupric ammonium ions, preferably in the proportion of about 30% by weight (based on the amount of zinc present) although lesser amounts of copper will still provide some benefits. Such cupric ammonium ions may be provided by dissolving copper oxide or copper carbonate in the ammoniacal zinc salt solution.

By another aspect of this invention, a second modified composition is provided in which the principal composition, or the first modified composition includes, additionally, up to about 10% by weight (total) of a vinyl polymer latex.

By yet another aspect of this invention, a third modified composition is provided in which the principal composition, or the first modified composition or the second modified composition includes, additionally, up to about 30% by weight (based on the amount of zinc present) of an acidic organic surfactant compound which is soluble in the ammoniacal salt solution.

By still another aspect of this invention, a fourth modified composition is provided, in which the principal composition, or the first, second or third modified composition includes, additionally, up to about 30% by weight (based on the amount of zinc present) of an additional fungicidal agent.

If the composition is to be used as a sealer primer, the presence of a surfactant is not necessary. However, the presence of suitable surfactants or wetting agents is of great importance in the application of these compositions by continuous spray application. Such continuous movement lines on which these treatments are carried out can move at a rate up to about 1200 feet a minute. The surfactants which are suitable for use in these compositions generally may be described as acidic organic compounds which are insoluble in water but which are solubilized by the ammoniacal salt solution. They are used to improve the wetting characteristics of the composition on wood and, where latex is also present, they are used to improve the stability of the polymer dispersion. These acidic organic compounds generally comprise aliphatic or aromatic compounds or halogenated derivatives thereof. The aliphatic compound generally has chains or loops of a length of about 10 to about 18 carbon atoms between acid groups. They may have complex structures in which there is more than one acidic group. Examples of such materials include the following: an ester of phosphoric acid, decanoic acid, a phenol, a chlorinated phenol, or a dimer acid formed from unsaturated fatty acids. Such surfactants will normally be present in solution as the salt of the zinc ammonia complex. In some cases, it may be desirable first to prepare a zinc salt of the organic acid before adding it to the composition. If a latex is present, the surfactant is generally added to the latex and then the two solutions are mixed. Unlike other compositions without latex, formulations containing the latex will require larger quantities of the surfactant, depending on the type of latex used.

Another optional ingredient in the composition of an aspect of this invention is a latex, which may be used to enhance the effectiveness of this composition. The latex generally has fine particle size, about 0.01 to about 0.1 microns, and a glass transition temperature below about ±5° C. The chemical composition is such taht the latex would form water repellent films and would be insolubilized on drying by reaction with the salt composition. They are, in general, vinyl polymer latices produced from monomers such as, for example, styrene, vinyl acetate, acrylic and methacrylic monomers. Preferably, the vinyl polymer is a copolymer of acrylic acid, methacrylic acid, acid esters of maleic acid, itaconic acid or acid esters of itaconic acid, as well as styrene-butadiene copolymers. Thus, for example, they include copolymers of styrene, vinyl acetate, acrylic monomer or methacrylic monomer with acrylic acid, methacrylic acid, acid esters of maleic acid, itaconic acid or acid esters of itaconic acid, or styrene-butadiene polymers or 2-ethylhexyl acrylate polymers.

For applications of this composition for protection of lumber during air-seasoning and in storage or transit, an additional fungicide may be added to enhance the fungicidal activity of the zinc itself or of the optionally added copper. The fungicides are characterized in that they are capable of forming insoluble salts or complexes with the zinc salts of the composition. They are used at levels which do not detract from the water repellent characteristics of the salt composition. Examples of these include hexamine (hexamethylenetetramine), chlorinated phenols, acids of arsenic, dimethylthiocarbamate, ammonium hydrosulfite, ethylenebis-thiocharbamate and ammonium thiocyanate.

The level of ammonia used in the above formulations is generally in excess of that required to form salts or coordinating complexes so that the aqueous compositions will have a pH of about 9 or higher. In addition the ratio of ammonia to zinc should be at least about 0.1 up to about 1. The non-volatile solids of the compositions may vary between about 2% and about 60%.

While it is not desired to be limited to any particular theory, it is believed that the high moisture pick-up of wood is due to physical absorption of moisture onto cellulose chains in the microfibrils, resulting in a decrease in the association between neighbouring cellulose chains. It is felt that the improvement in moisture pick-up of the treated wood is due to a cross-linking action by the metal ion between neighbouring cellulose chains. This cross-linking action could occur due to the high strength of coordination linkages. It is further believed that resistance to photodegradation is associated with the formation of pigment crystals formed within the wood substance which effectively screens the natural polymers from the damaging radiation.

DESCRIPTION OF PREFERRED EMBODIMENTS

Description of the Drawings

Brief Description of the Drawings

In the accompanying drawings,

FIG. 1 is a graph showing the contact angles of water on treated spruce, treated with various compositions, with contact angle (in degrees) as ordinate and time (in seconds) as abscissa;

FIG. 2 is a graph showing water pick-up on spraying on treated and untreated spruce, pine and cedar, with water pick-up (in grams) as ordinate and time (in hours) as abscissa; and FIG. 3 is a graph showing resistance to water uptake, on a spruce substrate treated with various compositions, with water uptake (as percentage of control) as ordinate, and water exposure (in hours) as abscissa.

DESCRIPTION OF THE EXAMPLES OF THE INVENTION

The invention in certain of its embodiments is illustrated in the following examples in which all proportions are by weight.

EXAMPLE 1.

Moisture Pickup

A treating solution according to one embodiment of this invention was prepared as follows: Zinc oxide and ammonium thiocyanate were mixed with concentrated (28%) aqueous ammonia solution and stirred to effect solution. Water was then added to achieve the following formulation:

| | |
|---|---|
| zinc oxide | 5 parts |
| ammonium thiocyanate | 10 parts |
| aqueous ammonia solution (2%) | 85 parts |

White spruce and white pine panels 2 × 8 × ½ were used in this example.

Matched pairs of panels were cut from the same piece of lumber. One of these was subjected to treatment and the other was used as a control specimen.

The treating solution was applied to the panels by three processes: (1) by spray; (2) by brush; and (3) by a 10 second dip.

Treated samples and controls were subjected to a 6 hour water spray in a Xenon Weather-Ometer. The moisture pickup on treated specimens was less than half that obtained with the untreated controls.

EXAMPLE 2

A treating solution according to one embodiment of this invention was prepared using the procedure described in Example 1, to provide a composition having the following formulation:

| | |
|---|---|
| zinc oxide | 9 parts |
| ammonium thiocyanate | 18 parts |
| copper carbonate | 1 part |
| aqueous ammonia (4%) | 72 parts |

Wood samples similar to those used in Example 1 were used in this Example.

The samples to be treated were pre-heated to a surface temperature of 100° C. They were then dipped for 10 seconds into the cold treating solution.

Moisture Pickup

Treated samples and untreated samples (controls) were subjected to a water spray for 6 hours.

The moisture pickup in the treated samples was less than 50% of that of the controls.

Erosion Resistance

Treated and untreated (control) samples were subjected to ultraviolet radiation using a mercury diffusion lamp placed 5 inches from the surface of the sample for a period of 80 hours.

The control samples suffered erosion of the surface to a depth of 1/32 to 1/16 in. in the springwood bands. No erosion was observed with the treated specimens.

Fungal Resistance

Treated and untreated (control) samples were inoculated with spores of the following fungi: Neurospora, *Aspergillus niger* and a mixture of molds (Neurospora, Penicillium and *Certocystis adiposa*.

The control samples showed growth of the fungi within 1 week. Treated samples showed no mold growth.

EXAMPLE 3

Moisture Pickup

A treating solution according to one embodiment of this invention was prepared using the procedure described in Example 2 to give the following formulation:

| | |
|---|---|
| zinc oxide | 5 parts |
| ammonium thiocyanate | 10 parts |
| AC34 (Trade Mark of Rohm & Haas for its acrylic latex) (20% solids) | 50 parts |
| aqueous ammonia (4%) | 35 parts |

Wood samples used in this Example were similar to those described in Example 1.

Test Method (A)

The samples to be treated were pre-heated to a surface temperature of 100° C. using infrared radiation and then were given two passes through a roller coater where the treating solution was applied (the application roll of the roller coater was covered by a lambs wool sleeve).

Test Method (B)

Samples to be treated were placed in a pressure vessel and were evacuated for 20 minutes. The treating solution was then introduced to the pressure vessel sufficient to cover the specimens to be treated. An over pressure of 100 lbs/sq. in. of air was applied and this pressure was maintained for 3 hours. The pressure in the treating vessel was then reduced to atmospheric pressure and the treating solution was removed.

Samples treated by method (A) and method (B) described above and control samples were subjected to 6 hours water spray in a Xenon Weather-Ometer. Regardless of the method of treatment, the moisture pickup of the treated samples was less than 50% of the moisture pickup of the control samples.

EXAMPLE 4

Wet Strength Increase of Paper

A treating solution according to one embodiment of this invention was the same as was used in Example 1. The sample tested was Whatman No. 1 filter paper (unsized). The paper was dipped for 1 second into the treating solution and dried.

Samples of treated paper and untreated paper were cut in size 0.5 inch × 5 inch strips and the wet tensile strength (in the machine direction) was determined according to Tappi Standards Method T456-OS68 for tissue products.

The wet strength of the treated paper was increased by more than 300 percent over that of the untreated paper. The average wet strength of the treated paper was 1.8 lb. as compared to 0.3 lb. for the untreated paper. This was equal to 28 percent of the dry strength of the untreated paper (6.5 lbs.).

EXAMPLE 5

Light Stability

The treating solution according to one embodiment of the present invention was an aqueous composition having the following formulation: ZnO, 20%; $NH_4CNS$, 40%; $NH_3$, 10%; decanoic acid, 0.2%. Spruce panels, brushed with the solution, showed no significant loss in weight as compared to a loss of 100 mg with untreated matched panels when exposed to light from a 500 watt Hg vapour lamp for 20 hours.

EXAMPLE 6

Siding Application as a Primer

The treating solution of one embodiment of the present invention as used herein was an aqueous composition having the following formulation: ZnO, 5%; $NH_4CNS$, 10%; $NH_3$, 1.5%; latex (small particle size butadiene-styrene latex), 5%; decanoic acid, 0.2%. The composition was applied to western red cedar panels as a primer-sealer and then the panels were top coated with a conventional exterior paint. Control panels were primed with diluted conventional exterior latex paint and then top coated with the same paint. After 200 hours in a Xenon Weather-Ometer, extractive staining was evident on the controls while no staining occurred with panels primed with the composition of this invention.

EXAMPLE 7

Control of Kiln Burn

The treating solution of one embodiment of the present invention as used herein was an aqueous composition having the following formulation: ZnO, 1%; $NH_4CNS$, 2%; $NH_3$, 1%; decanoic acid, 0.1%. Dip treatment of green white pine boards almost completely eliminated the brown stain conventionally produced during kiln drying of the boards. The results are shown below in the following table.

| Effect of Ammoniacal Zinc Oxide on Number of White Pine Boards with Brown Stain after Kiln Drying | | | | |
|---|---|---|---|---|
| Percent of Surface Stained | Rough Treated | Controls | Skip Planed Treated | Controls |
| 0 | 34 | 1 | 38 | 1 |
| 0 – 24 | 6 | 4 | 2 | 17 |
| 25 – 49 | 0 | 11 | 0 | 9 |
| 50 or more | 0 | 24 | 0 | 13 |

EXAMPLE 8

Reduction of Fungal Staining in Seasoning and Lumber Transit

The treating solution of one embodiment of the present invention as used herein was an aqueous composition having the following formulation: ZnO, 5%; $NH_4CNS$, 10%; $NH_3$, 1.5%; decanoic acid, 0.1%. Green pine skip-planed boards were dipped in the solution and sprayed with spores of fungi. These and matching controls were then placed in a tropical chamber (95% relative humidity at 70° F.) for 12 days and examined for mold and stain fungi growth. Molds and fungi grew luxuriantly on the controls while the treated boards were practically free from molds and fungal attack.

EXAMPLE 9

Water Repellency

The unexpected improvement in water repellency was determined by measuring the contact angle of various treated spruce panels. (The contact angle is a measure of water repellency, and is the term applied to the angle formed by water on the surface of a solid at the gas-solid-liquid interface, measured as the dihedral angle in the liquid.) The panels were treated with the following treating solutions: $ZN(CNS)_2$; $ZnCO_3$; zinc pentachlorophenol; $ZnAsO_4$; zinc pentaborate; $ZnPO_4$; and $ZnSO_4$. The results are shown graphically in FIG. 1.

It is seen that the treating composition of aspects of this invention has a surprising and unexpectedly much greater contact angle than the analogous treating agents of the prior art.

EXAMPLE 10

Water Pickup on Spruce, Pine and Western Red Cedar

Tests were also conducted on panels of spruce, pine and western red cedar, some of which had been treated with the treating composition of embodiments of this invention, and some of which were untreated, for controls and the amount of liquid water uptake in a Xenon Weather-Ometer was determined. It is seen from the graph in FIG. 2 that in 6 hours, the treated western red cedar panels took up approximately one-half as much water as the untreated, control panels and that the water takeup of treated spruce and treated pine is much less than that of untreated spruce and pine, respectively, and is even less than untreated cedar.

EXAMPLE 11

Water Pickup with Latex-containing Composition

The synergistic effect of the composition of another embodiment of this invention with, additionally a latex (e.g. a butadiene-styrene latex) was ascertained by determining the water takeup of a sample treated with the composition of this invention, and of a sample treated with the latex alone, and of a sample treated with the composition of this invention with, additionally, latex, as well as untreated control panels. The results are shown graphically in FIG. 3.

It is seen that while the panel treated with the composition of this invention took up about 75% of that taken up by the control, and while the latex treated panel took up about 60% of that taken up by the control, the composition of this invention with, additionally, the latex, took up only about 30%.

EXAMPLE 12

Comparison of Thiocyanate vs. Carbonate Systems

Dimension Stability

A treating solution of the thiocyanate system was prepared with the following composition:

| | |
|---|---|
| zinc oxide | 5 parts |
| ammonium thiocyanate | 10 parts |
| aqueous ammonia solution (3%) | 85 parts |

Another treating solution of the carbonate system was prepared with the following composition:

| | |
|---|---|
| zinc oxide | 5 parts |
| ammonium carbonate | 6 parts |
| aqueous ammonia solution (5%) | 89 parts |

Two sets of Douglas fir samples (2 × 2 × ½) were vacuum impregnated separately with the two systems and oven dried. These sets, along with an untreated control set, were then immersed in water for 24 hours and the extent of volumetric swelling was determined. The percent decrease in volume swelling from the untreated controls was found to be 37.19 percent for thiocyanate system as compared to 8.11 percent for the carbonate system.

Water Pickup

Two sets of spruce panels (9 × 2½ × ½) were dipped (30 secs) separately in the two solutions referred to in A. The oven dried samples were then exposed to water spray for 6 hours in a Weateer-Ometer and moisture pickup was determined. The average water pickup of a thiocyanate treated panel was 3.5 grams as compared to 5 grams for a carbonate treated panel.

Adhesion

Two sets of spruce panels were prepared as in B. After oven drying the panels, an acrylic latex coating was applied to the panels. After drying and conditioning for 7 days, cross-hatch adhesion test was carried out on the panels. Average area of adhesion failure was 4 percent for the thiocyanate system as compared to 14 percent for the carbonate system.

A summary of comparative test data is included in the following table.

| Test | Carbonate | Thiocyanate |
|---|---|---|
| (1) Dimension stability Decrease in swelling (%) | 8.11 | 37.19 |
| (2) Adhesion Cross-hatch test-failure (%) | 14 | 4 |
| (3) Water Pickup in 5 hrs (grams) | 50 | 35 |

It has been found that the composition of the present invention containing ammoniacal zinc thiocyanate is superior to other compositions of related applications Ser. No. 356,355 filed May 2, 1973 now U.S. Pat. No. 3,945,834, granted Mar. 23, 1976. This application is also related to copending application Ser. No. 362,104 filed May 27, 1973 now U.S. Pat. No. 3,945,835, granted Mar. 23, 1976. Thus, the compositions of the present invention show superior performance in adhesion, water repellency and dimensional stability. The thiocyanate system of the present invention requires much less ammonia and is compatible with a greater variety of latexes compared to the carbonate system.

A composition has thus been provided in which the durability of the treated wood or wood product is vastly improved without necessarily modifying the natural appearance of the wood or wood product. However, formulation changes are permitted which will enable desired colour changes to be introduced. Compositions are provided in which compatible polymer/salt mixtures can be used which, on drying, are believed to cross-link within the wood substance and interact with the wood substance to provide still further enhanced characteristics.

The treatments using compositions of aspects of this invention confer the advantages indicated to the following range of wood products: lumber, shingles and shakes, plywood, particle-board, fiber boards, and paper products.

The preceding examples can be repeated with similar success by substituting the generically and specifically described reactants and operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

We claim:

1. A wood treating composition comprising an aqueous solution containing:
   a. zinc ion, in a total amount, in the solution, of from about 0.5 to about 10% by weight, as zinc;

b. ammonium thiocyanate, in an amount of from about 1 to about 28% by weight, with the mole ratio calculated as $NH_4CNS/Zn$ being from about 2 to about 3; and c. ammonia, in an amount of from about 0.1 to about 28%, sufficient to provide a ratio of ammonia to zinc of at least about 0.1 to about 1, the composition having a pH of about 9 or more.

2. The wood treating composition of claim 1 comprising an aqueous ammoniacal solution of $Zn(CNS)_2$.

3. The wood treating composition of claim 2 wherein the amount of $Zn(CNS)_2$ is about 1 to about 25% by weight, and the aqueous ammoniacal solution is at a concentration of about 1 to about 28% by weight.

4. The wood treating composition of claim 3 including, additionally, copper ions.

5. The wood treating composition of claim 3 including, additionally, cupric ammonium ions, the proportion of said cupric ammonium ions being about 30% by weight (based on the amount of zinc present).

6. The wood treating composition of claim 3 including, additionally, cupric ammonium ions provided by dissolving copper oxide in the zinc salt solution.

7. The wood treating composition of claim 3 including, additionally, cupric ammonium ions provided by dissolving copper carbonate in the zinc salt solution.

8. A concentrated aqueous solution, containing (a) ZnO; (b) $NH_4CNS$; and (c) $NH_3$, wherein the mole ratio $NH_4CNS/Zn$ = about 2 to about 3; and the mole ratio $NH_3/Zn$ = at least about 0.1 to about 1.

9. The concentrate of claim 8 including, additionally, up to about 30% by weight (based on the amount of zinc present) of a surfactant compound which is soluble in said ammoniacal salt solution.

10. The concentrate of claim 8 including, additionally, up to about 30% by weight (based on the amount of zinc present) of an additional fungicidal agent.

* * * * *